United States Patent [19]

Kraus

[11] Patent Number: 5,571,728

[45] Date of Patent: Nov. 5, 1996

[54] METHOD FOR ANALYZING PARTICLE-ENHANCED AGGLUTINATION REACTIONS IN CENTRIFUGAL ANALYZERS BY DETERMINING THE BRIGHTENING OF TURBIDITY

[75] Inventor: Michael Kraus, Marburg, Germany

[73] Assignee: Behringwerke Aktiengesellschaft, Marburg, Germany

[21] Appl. No.: 41,210

[22] Filed: Apr. 1, 1993

[30] Foreign Application Priority Data

Apr. 4, 1992 [DE] Germany ............... 42 11 351.2

[51] Int. Cl.⁶ ............................................. G01N 33/546
[52] U.S. Cl. ............ 436/534; 436/501; 436/503; 436/523; 436/525; 436/531; 436/909; 435/5; 435/6; 435/7.1; 435/7.92; 435/13
[58] Field of Search ................ 436/534, 501, 436/503, 523, 525, 531, 534, 909; 435/7.1, 5, 6, 7.92, 7.93, 7.94, 7.95, 13

[56] References Cited

U.S. PATENT DOCUMENTS

| | | | |
|---|---|---|---|
| 4,118,192 | 10/1978 | Sawai et al. | 424/12 |
| 4,203,724 | 5/1980 | Sawai et al. | 436/518 X |
| 4,208,185 | 6/1980 | Sawai et al. | 436/518 X |
| 4,480,042 | 10/1984 | Craig et al. | 436/533 |
| 4,720,465 | 1/1988 | Jensen et al. | 436/523 |
| 4,721,681 | 1/1988 | Lentrichia et al. | 436/523 |
| 4,988,630 | 1/1991 | Chen et al. | 436/533 |
| 5,206,140 | 4/1993 | Marder et al. | 435/7.1 |

FOREIGN PATENT DOCUMENTS

| | | |
|---|---|---|
| 0080614A2 | 6/1983 | European Pat. Off. . |
| 0317796A1 | 5/1989 | European Pat. Off. . |
| 29 05 434 A1 | 8/1979 | Germany . |

OTHER PUBLICATIONS

Simo et al, "Automated Latex Agglutination Immunoassay of Serum Ferritin with a Centrifugal Analyzer", Clin. Chem. 40/4, 625–629 (1994).
W. Tanaka et al, "Discrete Chemistry Analyzers, Part I: batch Systems in Laboratory Instrumentation", Third Edition (J. P. Lippencott Company 1987) pp. 271–283.
Immunoturbidimetric Method for Routine Determinations of Apolipoproteins A–1 and B, Brustolin, et al., Clinical Chemistry, 37(5):742–747 (1991).
Immunoassay by Light Scattering Spectroscopy, Cohen et al., Immunochem. 12:349–351 (1975).
Latex Particle Agglutination in the Immunochemical System Human Serum Albumin—Anti–Human Serum Albumin Rabbit Serum, Dezelic et al., Eur. J. Biochem., 20:553–560 (1971).
A Photometric Method For The Determination of Serum Titres By Latex Particle Agglutination, Dezelic et al., Croatica Chemica Acta, 42:457–466 (1970).
Twelve–Protein Immunoassay Profile on The COBAS FARA, Hudson et al., J. Clin. Lab. Anal., 1:191–197 (1987).
A Sensitive Kinetic Latex Agglutination Immunoassay Adapted to Centrifugal Analysis, Lentrichia et al., J. Immun. Methods. 89:257:263 (1986).
Automated Nephelometric Immunoassays With Novel Shell/Core Particles, Kapmeyer et al., J. Clin. Lab. Anal., 2:76–83 (1988).
Light–Scattering Immunoassay of Specific Proteins: A Review, Price et al., Ann. Clin. Biochem., 20:1–14 (1983).

(List continued on next page.)

*Primary Examiner*—Carol A. Spiegel
*Attorney, Agent, or Firm*—Finnegan, Henderson, Farabow, Garrett & Dunner, L.L.P.

[57] ABSTRACT

The invention relates to a method for determining analytes, in which a sample of a biological material which possibly contains this analyte is incubated with at least one binding partner which is specific for the analyte and which is immobilized on a particulate carrier material, and the change in turbidity brought about by the analyte is determined.

10 Claims, 6 Drawing Sheets

OTHER PUBLICATIONS

Immunoassay of $\alpha_1$-Acid Glycoprotein in The Cobas Bio Centrifugal Analyzer, Verme et al., Clin. Chem., 34(11):2316–2320 (1988).

Evaluation of Kinetic Light Scattering as an Approach to the Measurement of Specific Proteins With The Centrifugal Analyzer. II. Theoretical Considerations, Buffone et al., Clin. Chem. 21(12):1735–1746 (1975).

Patent Abstract of Japan, vol. 12, (307): 124 (Aug. 1988) and JP-A-63 078 066 (Yatoron KK) Apr. 8, 1988.

METHOD FOR ANALYZING PARTICLE-ENHANCED AGGLUTINATION REACTIONS IN CENTRIFUGAL ANALYZERS BY DETERMINING THE BRIGHTENING OF TURBIDITY

The invention relates to a method for determining analytes, in which a sample of a biological material which possibly contains this analyte is incubated with at least one binding partner which is specific for the analyte and which is immobilized on a particulate carrier material, and the change in turbidity brought about by the analyte is determined.

Immunochemical detection methods for the quantitative and qualitative determination of substances of therapeutic and/or diagnostic importance are based on the solid-phase principle in which a binding partner (for example antibody, antigen, substrate and substrate analogs, enzymes, lectins) which has affinity for the analyte to be detected is immobilized on a water-insoluble carrier (solid phase). Used as solid phases are various water-insoluble polymers which are employed in various geometric embodiments such as tubes, spheres or microtiter plates.

So-called heterogeneous immunoassays, for example ELISA, permit, owing to the formation of complexes composed of the analyte with the immobilized binding partner, the removal of unbound analytes. In a subsequent detection step, the immobilized analyte is determined quantitatively. However, these methods are labor-intensive and time-consuming.

In the so-called homogeneous methods, use is made predominantly of nephelometric or turbidimetric methods. The kinetics of the formation of AB from analyte (A) and binding partner (B) can be followed by the change which occurs in the scattering or absorption of the incident light. When suspendible particles such as, for example, latex particles, on which a binding partner is immobilized, are used, there is an enhancement of the effects, which makes it possible to determine considerably lower analyte concentrations. These homogeneous methods can be carried out quickly and simply and they permit, in particular, the automation of sample analyses.

The designation AB is not intended to indicate a composition of amounts in a defined stoichiometric ratio to one another but rather represents the product (AB) resulting from the reaction of analyte (A) and binding partner or immobilized binding partner (B).

Particle-enhanced, turbidimetric immunoassays of this type are described, for example, in the patent DE 29 05 434. The particles used therein have a diameter <1.6 µm and are employed in concentrations of 0.05–1% in the solution to be investigated. Ideally according to this patent, the reaction kinetics are followed at wavelengths which are at least 1.5 times the particle diameters. The turbidity measured in the solution shows an optimum depending on the particle size: as the particle size increases there is an initial increase in turbidity but it decreases again when the particles are very large (see also: Malinski, J. A. and Nelsestuen, G. L., "Relationship of turbidity to the stages of platelet aggregation." Biochim. Biophys. Acta 882:177–182 (1986)). The decrease in turbidity is attributable to the fact that when the particle size approaches the wavelength of the incident light the scattering in the direction of the light path increases and therefore an optical brightening is simulated in turbidimetric methods. This effect is suppressed in nephelometric methods by shuttering out the scattered light which is directed forwards.

In turbidimetric methods it has to date been almost exclusively the increase in absorption, that is to say the ascending part of the underlying function, that has been used for determining analyte concentrations (see, for example: Brustolin D. et al. "Immunoturbidimetric method for routine determinations of apolipoproteins A-1 and B.", Clin. Chem. 37(5), 742–747 (1991)). To avoid the effect of the light scattering in the forward direction it is therefore preferentially long wavelength light that is used, such as, for example, > 600 nm in the cited patent DE 2 905 434.

Determination of AB by use of the brightening reaction (descending part of the function) has been described only a few times (for example by Dezelic, G. J. et al., "Latex Particle Agglutination in the Immunochemical System Human Serum Albumin/Anti-Human Serum Albumin Rabbit Serum", Eur. J. Biochem. 20(4), 553–560 (1971)). However, the described method requires for determination of the rate of decrease of turbidity very low concentrations of the sensitized latex in the range from 0.007 to 0.028%. Because of these low concentrations it is necessary to remove impurities which cause turbidity. This and the low latex concentration means that the antigen-antibody reaction is unavoidably diminished and therefore measurement times of 18 to 20 h are necessary. The resulting precision, reproducibility and sensitivity of these methods are inadequate for determining concentrations of antigens or antibodies (Cohen, R. J. and Benedek G. B., "Immunoassay by Light Scattering Spectroscopy", Immunochem. 12, 349–351 (1975)).

The development of centrifugal analyzers in clinical chemistry has led to turbidimetric assays being adapted for these devices, which allow automatic processing and thus better precision of measurement too. The methods employed in these devices to date have also been only those in which the analyte is determined turbidimetrically through the increase in absorption caused by AB formation (see, for example, Gail A. Hudson et al., "Twelve-protein immunoassay profile on the Cobas Fara", J. Clin. Lab. Anal. 1, 191–197 (1987)).

Lentrichia and Yeung ("A sensitive kinetic latex agglutination immunoassay adapted to centrifugal analysis", J. Immunol. Meth. 89, 257–263 (1986)) have published a method for the competitive determination of HCG in a centrifugal analyzer, in which the authors observed a decrease in the measured signal about 6 min after the usual increase in absorption. This descending part of the reaction kinetics was used to adapt an HCG assay with commercially available latex reagents (particle diameter 220 nm). The determination was carried out at a wavelength of 690 nm, and the latex concentration in the assay mixture was 0.09%. The measurement time in this method is, however, about 30 min and is thus inferior to current turbidimetric methods which, as a rule, require only about 3 to 5 min. In addition, the mixed reaction kinetics (initial increase in the signal, then decrease) means there is a risk of errors in measurement: non-specific turbidities, for example, lead to an extension of the ascending portion of the reaction kinetics and thus, in some circumstances, even to a negative signal. This is why it was not possible to start the measurement until 8 min after the start of the reaction. This method, which is designated state of the art hereinafter, is thus still unsatisfactory.

The object on which the invention was based was now to find a photometric method which can be used to determine quantitatively, with great precision and reproducibility, the concentration of an analyte through the kinetics of formation of AB in automatic centrifugal analyzers known per se, and specifically within the time of about 3–8 min which is customary with such automatic devices (from addition of sample to output of results).

It has been found, surprisingly, that, under suitable reaction conditions, it is even possible to measure the decrease in turbidity immediately after the completion of the mixing and distribution phase caused by addition of the sample, and an unambiguous result can be obtained after about 2–7 min.

Without wishing to restrict the Subject-matter of the invention by stating the mechanism of the reaction, the following points appear to have a beneficial effect for the purpose of the invention on the kinetics of formation of AB:

1. an increase in the centrifugal acceleration or the use of particles of higher density, for example composed of magnetite,
2. the use of particles which are as spherical as possible in order to reduce the Stokes radius, and by additions to the medium which lead to a higher density, such as, for example, glycerol, polyethylene glycol,
3. an increase in the particle density in the mixture and of the density of loading on the sensitized particles.

It has emerged, surprisingly, that the use of particle concentrations which are higher than those used in the state of the art leads to a very rapid onset of the brightening which takes place in the analyzed solution, in contrast to the behavior described in the state of the art. The rate and the extent of the decrease in absorption depends on the concentration of the analyte in the investigated solution.

The invention thus relates to a method for determining analytes, in which a sample of a biological material which possibly contains this analyte is incubated with at least one binding partner which is specific for the analyte and which is immobilized on a particulate carrier material, and a) the reaction takes place under the influence of a centrifugal acceleration which is constant during the course of the measurement and which is preferably between 10 and 10,000 x g, particularly preferably 100–2,000 x g, very particularly preferably 800–1,200 x g,
b) the particle density in the mixture for measurement is at least 0.1% by weight,
c) the brightening in turbidity which occurs is measured immediately after the completion of the mixing and distribution phase caused by addition of the sample and
d) the concentration of the analyte is unambiguously determined by comparing the brightening in turbidity measured for the sample with values, measured under identical conditions, for samples of known analyte content.

Moreover, a preferred method is one in which analyte and specific binding partner are partners in an immunochemical reaction, and a particularly preferred method is one in which a specific binding partner is an antibody against a protein or a peptide from the coagulation, fibrinolysis or complement system, and a very particularly preferred specific binding partner is an antibody against the fibrin degradation product D dimer. Antibodies for the purpose of this invention are poly- and monoclonal antibodies as well as antibody fragments and modified antibodies such as, for example, bispecific antibodies.

A further preferred method is one in which particulate, natural and/or synthetic polymers which are as spherical as possible are used as carrier material, and particularly preferred as particulate carrier material are styrene/methacrylic acid or methacrylate/methacrylic acid copolymers.

A preferred method is also one in which the reaction takes place in a buffered medium with defined density and viscosity.

A preferred method is additionally one in which the change in the absorption can be followed at an angle of 0° to 180° to the direction of sedimentation.

A preferred method is furthermore one in which wavelengths from the range from 280 to 900 nm are used for measuring the change in absorption.

The invention also relates to the use of particulate carrier material coated with an analyte-specific binding partner in a method of this type, where the particle concentration in the mixture for measurement is higher than 0.09% by weight.

When particle concentrations according to the state of the art are used, as carried out, for example, in Example 2 (FIGS. 1 and 2) with 0.0125% by weight in the reaction solution, the agglutination reaction takes the described course: Depending on the analyte concentration there is an initial proportional increase in the turbidity of the solution. These reaction kinetics were found with a commercially available reagent for nephelometric determination of IgE (FIG. 1) and with a latex reagent, prepared by us, for determination of D dimer (as carried out in Example 1). The particle diameters were 230 nm in each case.

If, however, according to the present invention the particle densities used are above the concentration of 0.09% used in the state of the art, substantially only a decrease in turbidity is now to be recorded. The range in this connection is preferably from 0.1 to 1, particularly preferably from 0.1 to 0.4, very particularly preferably from 0.1 to 0.2% by weight. Comparison with a latex concentration according to the state of the art is shown by way of example in FIG. 3 (Example 3) for the D dimer latex reagent. FIGS. 4 (for the IgE latex reagent) and 5 (for the D dimer latex reagent) demonstrate that with a higher particle concentration according to the present invention, for example 0.1%, in the reaction solution (Example 4) the reaction kinetics are sufficiently constant after only about 1 min that measurements are possible within 5 min.

Owing to the mixing processes in the reaction cuvette of centrifugal analyzers it is normally possible to carry out measurements only with a certain time lag after sample addition.

For determination of the analyte concentration, it is possible to choose the kinetic method, i.e. the rate of decrease in absorption, the endpoint method, i.e. determination of the absolute difference in absorption after a chosen time, or the threshold method, i.e. determination of the time until a particular change in absorption has occurred. These possibilities are demonstrated by way of example in Example 6 in Tables 1 and 2.

Surprisingly, comparison of turbidimetric methods with an increase in turbidity and the method according to the invention (comparison of FIGS. 1 and 4, and of FIGS. 2 and 5) showed that the absolute changes in the absorption in the method according to the invention are a factor of 3 to 5 higher, which is, as a rule, associated with a corresponding improvement in the accuracy of measurement, which represents a great advantage of the method according to the invention.

Surprisingly, it also emerged, that the sedimentation rate can likewise be enhanced by the increase in the coating density. The determination, which is carried out in Example 5 for example, of D dimer with particles of different loading density shows, as depicted in FIG. 6, that the sedimentation rate increases at high loading densities. The increased reactivity of the latex reagent also means, however, an increase in turbidity at the start of the reaction, which must be compensated by a corresponding adjustment of the particle concentration, as carried out in Example 3.

It has furthermore emerged, surprisingly, that the determination according to the invention of analyte concentrations does not depend on the construction of the measurement optics in the centrifugal analyzer. The centrifugal analyzers used in Example 6 are mentioned as extreme cases. Whereas in one (for example Cobas Bio) the light path is arranged antiparallel to the direction of sedimentation, in the other extreme case (for example ACL 300) the turbidity is measured at right angles to the direction of sedimentation. Determination of the analyte concentration by the method according to the invention is possible in both methods. It may thus be assumed that the method according to the invention is applicable to all centrifugal analyzers.

In Example 6, determination of D dimer was carried out for comparison in media of different density (buffer solution, serum, plasma). The density effect leads to only slight differences in the results (Tables 1 and 2) so that this method can also be applied to different biological fluids without difficulty.

The method is suitable for all analyzers which measure the optical density of the mixture of sample and reagent before, after and/or during the centrifugation.

The centrifugal acceleration is preferably from 10 to 10,000 x g, particularly preferably from 100 to 2,000 x g, very particularly preferably 800–1,200 x g, and the optimal centrifugal acceleration shows a certain dependence on the particle density.

It is possible to determine, as measure of the aggregate formation, for example the time until the absorption in the assay mixture has undergone a preset change (threshold method). Another method comprises determining the decrease in absorption continuously, and evaluating the rate of decrease in absorption (kinetic method). Finally, it is also possible to use the difference between the absorption after a certain time and the initial value for the evaluation (endpoint method).

Suitable water-insoluble carriers (solid phase) are the natural and synthetic organic and inorganic polymers which are sufficiently known to the person skilled in the art, such as, for example:

polystyrene, polydextrans, polypropylene, polyvinyl chloride, polyvinylidene fluoride, polyacrylamide, agarose, latex, magnetite, porous glass powder, erythrocytes, leukocytes; or styrene/butadiene, styrene/methacrylic acid or methacrylate/methacrylic acid copolymers, and mixed polymers are also suitable.

The carriers are suitably in particulate form. Polystyrene spheres or latex spheres are particularly suitable as solid phase for the affinity binding partner.

The particles preferably have diameters between 0.1 and 1 μm, particularly preferably diameters between 0.1 and 0.3 μm.

The affinity binding partner on the carrier material is preferably a biological substance, for example an antigen, an antibody, a hapten, a lectin, a substrate analog, a protease inhibitor or a protease or inactive mutants thereof. Antibodies or antigens are preferred in this connection.

The concentration of the particles is chosen so that an optical density of 5 is not exceeded at the start of the measurement. An optical density between 1 and 3 is preferred.

A wavelength between 280 and 900 nm is preferably chosen for the detection. It is particularly preferable to use a wavelength like that used in generally customary chromogenic assays and available on clinical chemistry analyzers, for example at 390, 405, 490, 540, 630 nm. A wavelength of 405 nm is very particularly preferred. Bichromatic measurement methods are also preferred.

The assay mixture is composed of the sample and the reagent, and of a reaction medium. The reaction medium can contain the inorganic and organic substances which are known to the person skilled in the art and which serve to produce an environment which promotes the reaction, such as, for example, pH-buffering substances, for example phosphate, tris(hydroxymethyl)aminomethane, substances which influence the density and viscosity, for example polyethylene glycol, glycerol, or substances which minimize interference by lipids, for example detergents, or rheumatoid factors, for example gamma-globulin fractions. The reaction medium is preferably composed of a physiological NaCl solution.

The determination is preferably carried out at +10° to 40° C., particularly preferably at +20° to +40° C., very particularly preferably at +37° C.

The method according to the invention is distinguished by its simplicity, the ease of automation and a precision of measurement which is improved in comparison with the turbidimetric methods hitherto disclosed.

The following examples are intended to describe the invention in detail but not to restrict it in any way.

The percentages stated in the examples for the particle concentrations are in each case percentages by weight.

EXAMPLE 1:

Preparation of a latex reagent for the determination of fibrin fragment D dimer

Latex reagents were prepared by the method of W. H. Kapmeyer et al., "Automated nephelometric immunoassays with novel shell/core particles", J. Clin. Lab. Anal. 2, 76–83 (1988). A monoclonal antibody against D dimer (MAb DD5, Behringwerke AG, Marburg, FRG) was coupled to the dipentyl acetal groups of the graft copolymer in the ratio from 1:67 to 1:29 based on the weight of the reactants.

1 ml of the graft copolymer (4%) was mixed with 0.1 ml of an MAb DD5 solution (1 mg/ml; corresponds to a coupling ratio of 1:40) and 0.05 ml of a 20% strength aqueous TWEEN 20 detergent solution. The latex was activated by adjusting the solution to a pH of 2 with about 0.01 ml of a 1N HCl solution. After incubation at room temperature for 30 minutes, 0.25 ml of a saturated sodium hydrogen phosphate solution (pH 6.5) and 0.25 ml of an aqueous sodium borohydride solution (25 mg/ml) were added and vigorously mixed. The antibody was coupled to the activated aldehyde groups at room temperature for 1 h. Subsequently, the anti-D dimer latex conjugate was centrifuged (Beckman centrifuge, 40000 x g, 30 minutes) and the pellet was resuspended in 1.5 ml of a 0.1 molar glycine buffer (pH 8.2, containing 0.17M NaCl and 0.5% TWEEN 20 detergent). The solution was treated with ultrasound for about 5 sec (Branson Sonifier B 15). This stock solution was stored at +4° C. Working solutions with concentrations of 0.025 to 0.2%, based on the latex solids content, were prepared by diluting the stock solution with physiological saline solution (corresponds to 0.0125–0.1% in the reaction solution).

EXAMPLE 2:

Kinetics of the turbidity signals on use of latex reagents in methods hitherto customary A commercially available latex reagent for nephelometric determination of IgE in serum and an IgE standard serum with a concentration of 512 IU/ml (NA-latex-IgE reagent, Behringwerke AG, Marburg, FRG) were reconditioned with distilled water in accordance with instructions. The IgE standard was employed undiluted and in dilutions with physiological saline solution. A D dimer latex reagent prepared as in Example 1 with a coupling ratio of 1:40 was diluted with physiological saline solution to a concentration of 0.025%. A D dimer standard (Behringwerke AG, Marburg, FRG) was diluted with physiological saline solution to concentrations from 62.5 to 500 µg/l. Physiological saline solution was used as reaction medium.

The measurement was carried out in a centrifugal analyzer (Cobas Bio model, F. Hoffmann La Roche & Co. AG, Basle, Switzerland). 40 µl of sample and 5 µl of reaction medium were introduced. After 10 sec, 40 µl of latex reagent were added. The reaction was started by mixing the samples by centrifugation. At a constant centrifugation speed of about 1000 x g, the absorption at 405 nm was measured at intervals of 10 sec for a period of 5 min.

The absorption at the start of the measurement was about 0.8 units. The change from the initial absorption signal at 405 nm over the measurement period is depicted in FIG. 1 for the IgE latex reagent and in FIG. 2 for the D dimer latex reagent.

EXAMPLE 3:

Dependence of the reaction kinetics on the particle density in the mixture for measurement An anti-D dimer latex reagent prepared as in Example 1 with a coupling ratio of 1:40 was diluted with physiological saline solution to concentrations of 0.025, 0.1 and 0.2%. A D dimer standard (Behringwerke AG, Marburg, FRG) was diluted with physiological saline solution to a concentration of 250 µg/l. Physiological saline solution was used as reaction medium.

The change in absorption was determined in a centrifugal analyzer as described in Example 2. The extinctions at the start of the measurement were 0.8, 1.4 and 1.8 units at 405 nm. The course of the change determined in the absorption is depicted in FIG. 3.

EXAMPLE 4:

Course of the turbidity signals on use of latex reagents in the method according to the invention A lyophilized IgE latex reagent (NA-latex-IgE reagent, Behringwerke AG, Marburg, FRG) was reconditioned with only ⅓ of the normally used amount of distilled water. An anti-D dimer latex reagent prepared as in Example 1 with a coupling ratio of 1:40 was diluted with physiological saline solution to a concentration of 0.2%. IgE and D dimer standards were used as described in Example 2.

The change in absorption was determined in a centrifugal analyzer as described in Example 2. The extinctions at the start of the measurement were about 1.8 units at 405 nm. The course of the change determined in the absorption at various antigen concentrations is depicted in FIG. 4 for the IgE and in FIG. 5 for the D dimer latex reagent.

EXAMPLE 5:

Dependence of the reaction kinetics on the loading density of the latex reagent

Anti-D dimer latex reagents prepared as in Example 1 with coupling ratios of 1:67, 1:40 and 1:29 were diluted with physiological saline solution to a concentration of 0.2%. A D dimer standard (Behringwerke AG, Marburg, FRG) was diluted with physiological saline solution to a concentration of 125 µg/l. Physiological saline solution was used as reaction medium.

The change in absorption was determined in a centrifugal analyzer as described in Example 2. The absorption of the solution at the start of the measurement was about 1.8 unit at 405 nm. The course of the change determined in the absorption with latex reagents differing in antibody loading is depicted in FIG. 6.

EXAMPLE 6:

Determination of D dimer in phosphate buffer, serum and plasma in a centrifugal analyzer with measuring beam arranged at right angles to the direction of sedimentation.

The latex reagent coated as in Example 1 (coupling ratio 1:29) was diluted in phosphate-buffered, isotonic sodium chloride solution (PBS) to a working concentration of 0.2%. D dimer antigen (Behringwerke AG, Marburg, FRG) was added to PBS or a pool of serum or plasma from normal blood donors so that the final concentrations were 0, 313, 625, 1250, 2500 and 5000 µg/l. PBS was used as reaction medium.

Measurement was carried out in a centrifugal analyzer of the type ACL 300 from Instrument Laboratory, Milan, Italy. In this analyzer, the measurement beam passes through the sample solution at right angles to the direction of sedimentation. 20 µl of sample (PBS, serum or plasma) and 80 µl of reaction medium were introduced and mixed by centrifugation. After 30 sec, 50 µl of latex reagent were added by a pipette. The reaction was subsequently carried out at about 800 x g. The measurement was carried out continuously at 405 nm for 10 min.

The apparatus determines the decrease in light absorption by comparison with an apparatus-specific reference solution and presents the results in positive notation. The evaluation by various methods (endpoint, kinetic and threshold method) is detailed in Table 1. The time found until a decrease in absorption of 0.1 has occured is inversely proportional to the D dimer concentration. The rate of decrease in absorption, or the total decrease in absorption at the end of the measurement is directly proportional to the D dimer concentration in the sample. The results of the method both in PBS and in serum and plasma are in agreement.

Table 1

Table 1 shows the dependence of the changes in absorption in a centrifugal analyzer with light path at right angles to the direction of sedimentation.

TABLE 1

| D dimer (µg/l) | PBS | Serum | Plasma |
| --- | --- | --- | --- |
| Endpoint method: Absorption (t = 0 sec) − absorption (t = 300 sec) | | | |
| 0 | −0.013 | −0.004 | 0.003 |
| 313 | 0.194 | 0.185 | 0.213 |
| 625 | 0.423 | 0.406 | 0.447 |
| 1250 | 0.702 | 0.629 | 0.627 |
| 2500 | 0.874 | 0.775 | 0.748 |
| 5000 | 0.926 | 0.838 | 0.796 |
| Kinetic method: Change in absorption per min in [−1/min] | | | |
| 0 | 0.005 | 0.005 | 0.005 |
| 313 | 0.068 | 0.069 | 0.119 |
| 625 | 0.207 | 0.192 | 0.205 |
| 1250 | 0.296 | 0.245 | 0.254 |
| 2500 | 0.324 | 0.273 | 0.281 |

TABLE 1-continued

| D dimer (µg/l) | PBS | Serum | Plasma |
|---|---|---|---|
| 5000 | 0.333 | 0.295 | 0.298 |
| Threshold method: Time until the change in absorption is <−0.1 [sec] | | | |
| 0 | >600 | >600 | >600 |
| 313 | 389 | 416 | 431 |
| 625 | 327 | 347 | 349 |
| 1250 | 289 | 301 | 306 |
| 2500 | 264 | 279 | 289 |
| 5000 | 259 | 271 | 278 |

EXAMPLE 7

Determination of D dimer in phosphate buffer and plasma in a centrifugal analyzer with measurement beam arranged antiparallel to the direction of sedimentation.

The D dimer latex reagent coated as in Example 1 (coupling ratio 1:29) was adjusted to a working concentration of 0.2% in phosphate-buffered isotonic sodium chloride solution (PBS). This corresponds to an absorption of about 1.8 at a wavelength of 405 nm. D dimer antigen (Behringwerke AG, Marburg, FRG) was added to PBS or a pool of plasma from normal blood donors so that the final concentrations were 0, 62.5, 125, 250, 500, 1000 and 2000 µg/l. PBS was used as reaction medium.

The measurement was carried out in a centrifugal analyzer of the type Cobas Bio (F. Hoffmann La Roche & Co. AG, Basle, Switzerland) as described in Example 2. In this analyzer, the measurement beam runs antiparallel to the direction of sedimentation.

Evaluation by the endpoint, kinetic and threshold method is detailed in Table 2. The time found until a decrease in absorption of 0.05 has occurred is inversely proportional to the D dimer concentration. The rate of decrease in absorption, or the total decrease in absorption at the end of the measurement is directly proportional to the D dimer concentration in the sample. The results of the method in PBS and plasma are in agreement.

Table 2

Table 2 shows the dependence of the changes in absorption in a centrifugal analyzer with light path antiparallel to the direction of sedimentation.

TABLE 2

| D dimer (µg/l) | PBS | Plasma |
|---|---|---|
| Endpoint method: Absorption (t = 0 sec) − absorption (t = 300 sec) | | |
| 0 | 0.022 | 0.020 |
| 62.5 | 0.045 | 0.075 |
| 125 | 0.059 | 0.131 |
| 250 | 0.197 | 0.205 |
| 500 | 0.272 | 0.250 |
| 1000 | 0.341 | 0.321 |
| 2000 | 0.343 | 0.347 |
| Kinetic method: Change in absorption per min in [−1/min] | | |
| 0 | 0.0028 | 0.0040 |
| 62.5 | 0.0087 | 0.0172 |
| 125 | 0.0148 | 0.0284 |
| 250 | 0.0359 | 0.0422 |
| 500 | 0.0485 | 0.0552 |
| 1000 | 0.0773 | 0.0884 |

TABLE 2-continued

| D dimer (µg/l) | PBS | Plasma |
|---|---|---|
| 2000 | 0.0755 | 0.0967 |
| Threshold method: Time until the change in absorption is <−0.05 [sec] | | |
| 0 | >300 | >300 |
| 62.5 | 300 | 200 |
| 125 | 240 | 120 |
| 250 | 80 | 70 |
| 500 | 50 | 50 |
| 1000 | 40 | 40 |
| 2000 | 30 | 40 |

Figure 1:
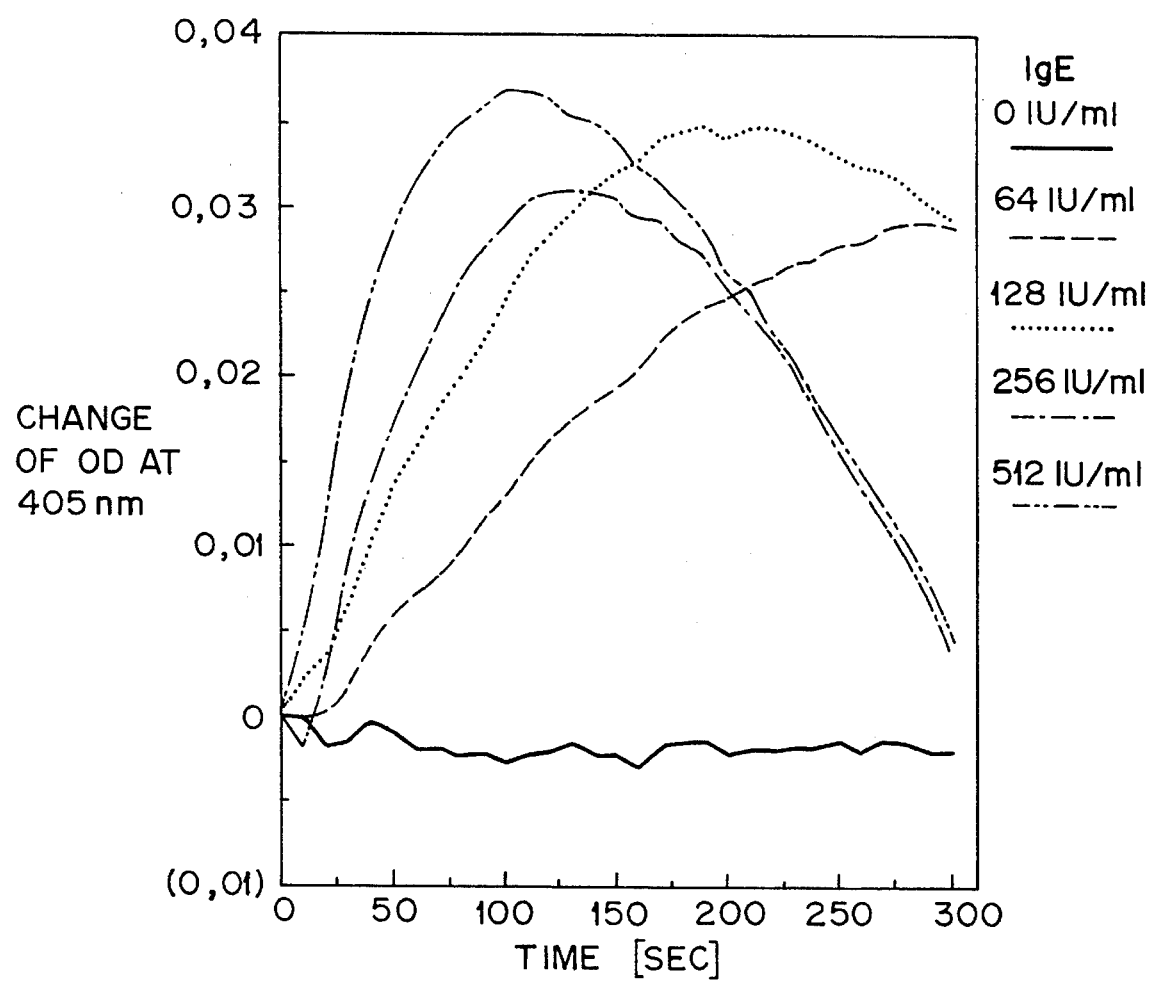
FIG. 1.
Figure 2:
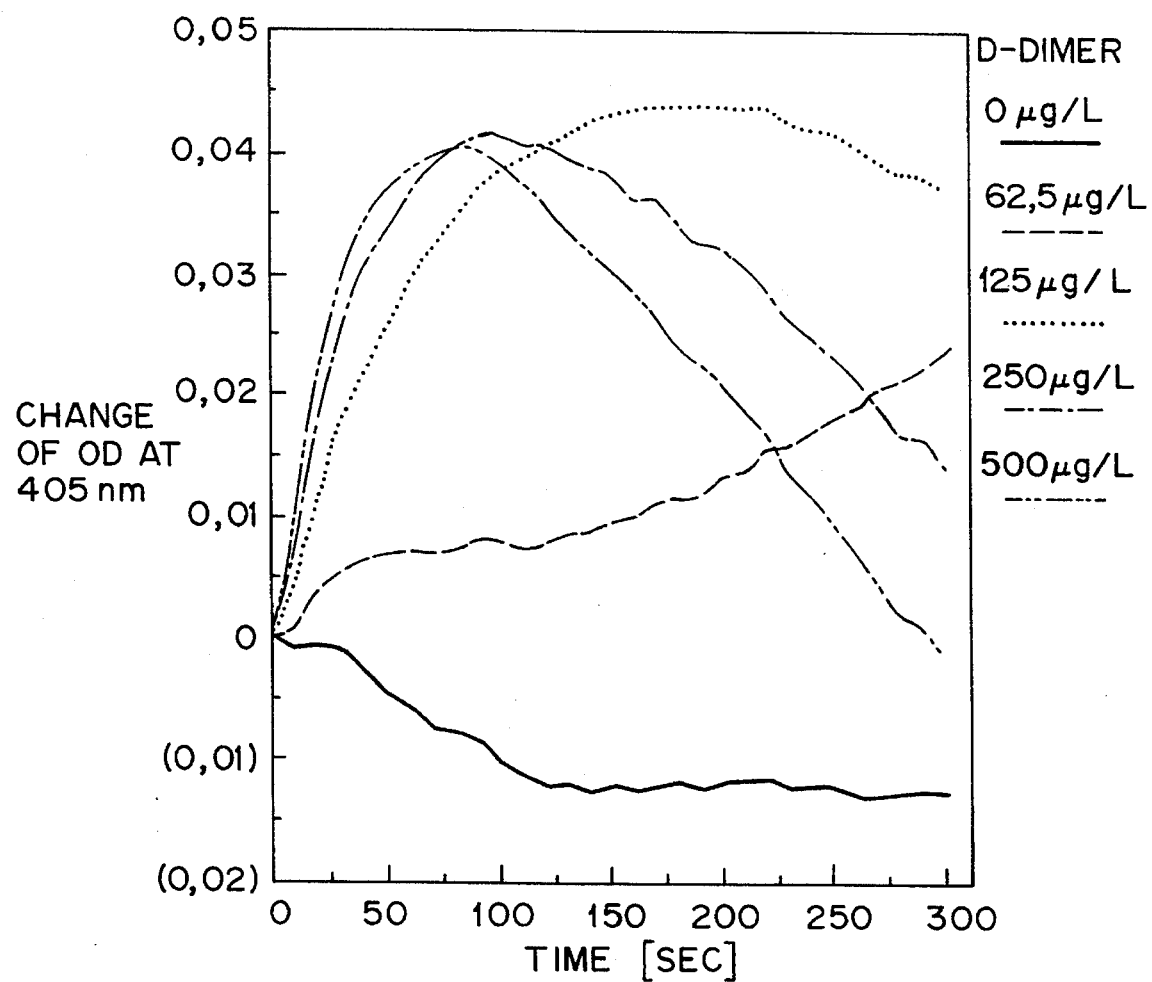
Figure 3:
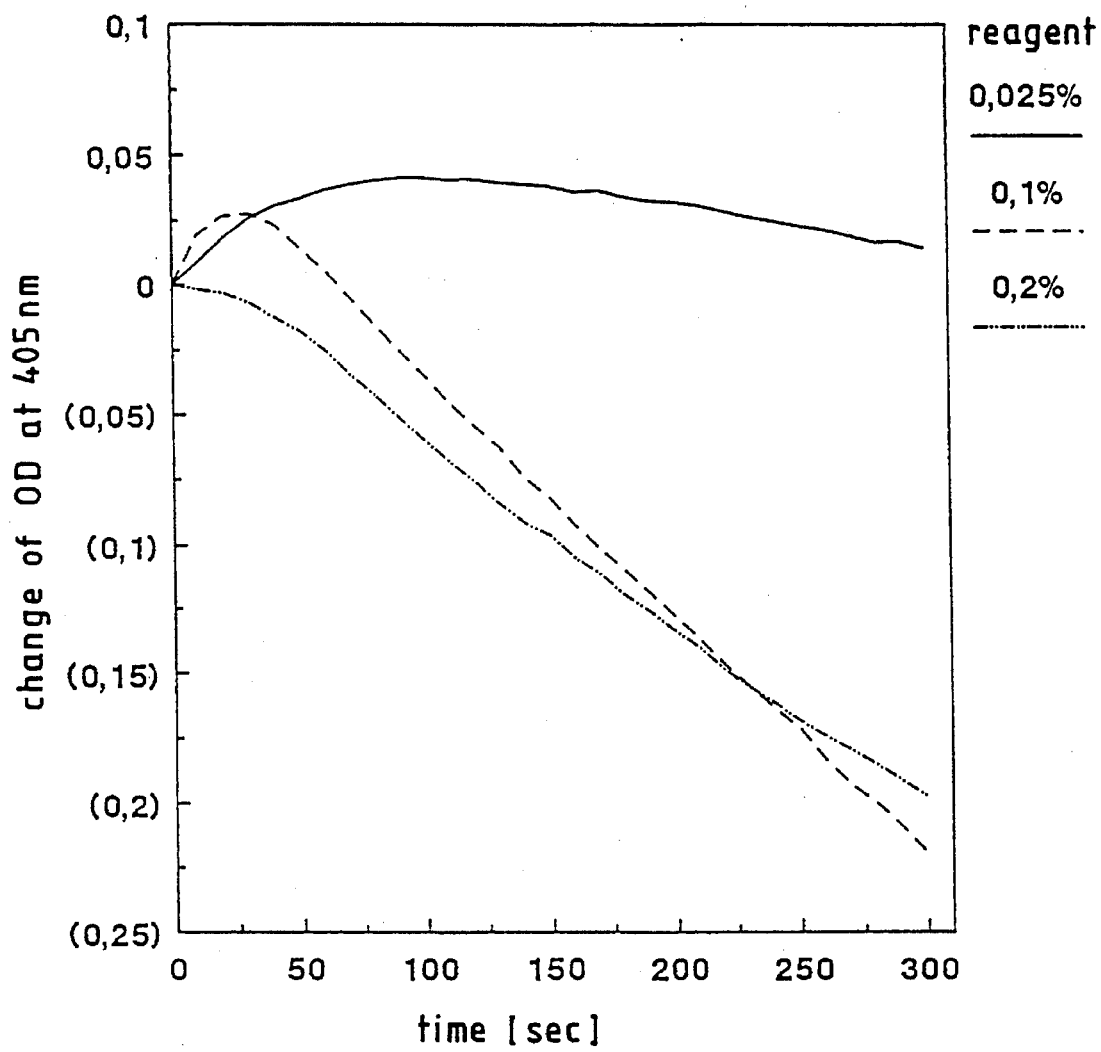
Figure 4:
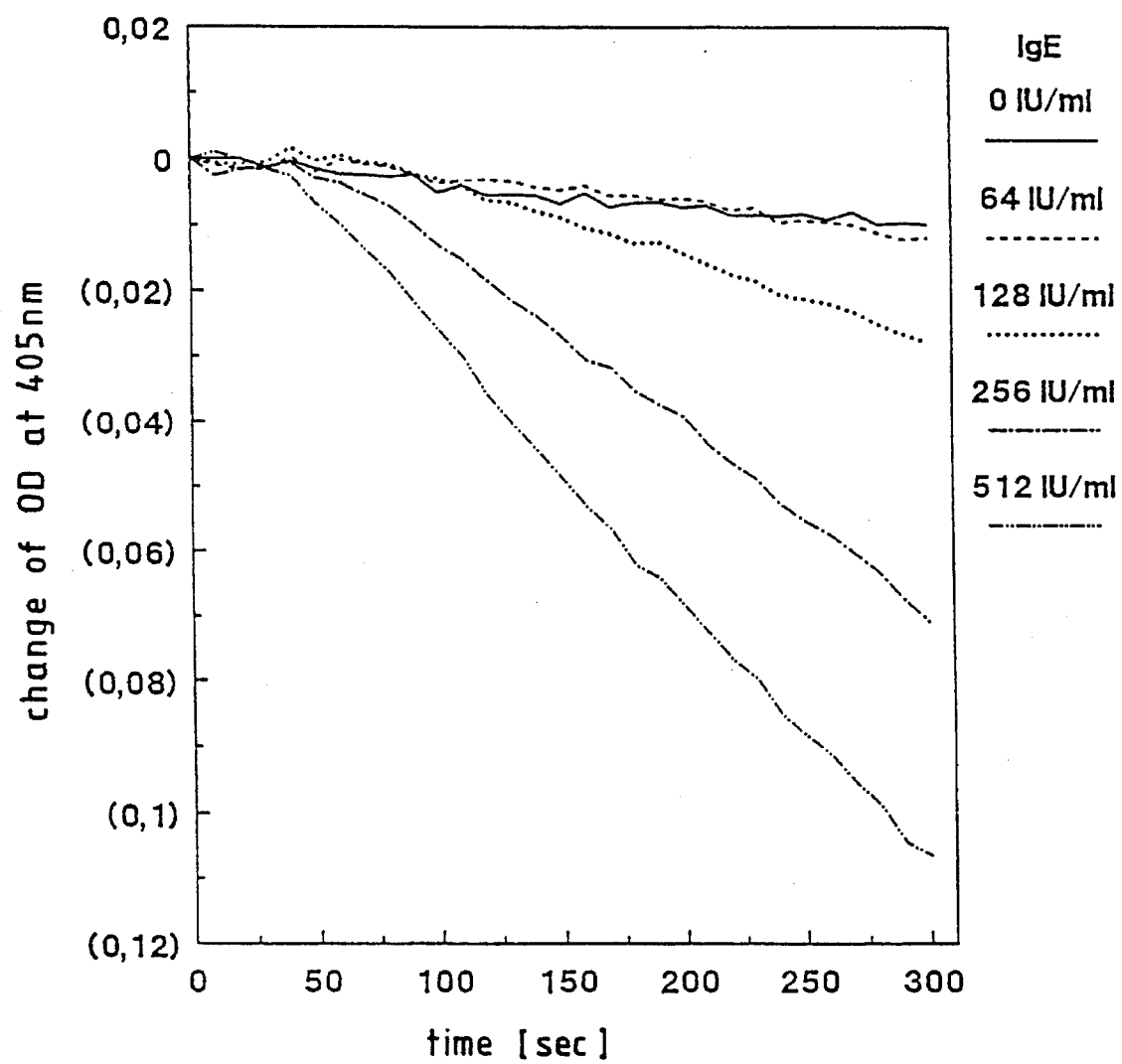
Figure 5:
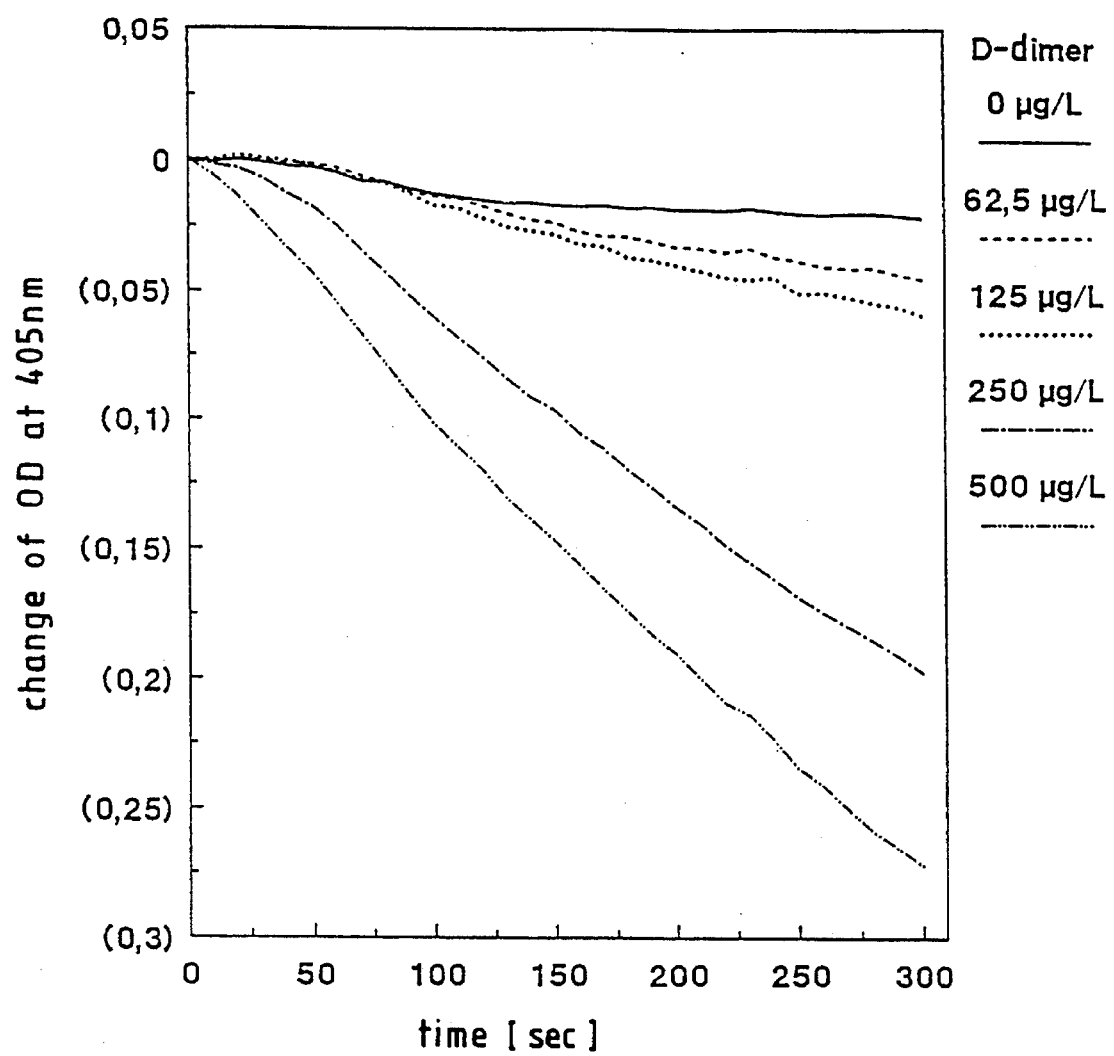
Figure 6:
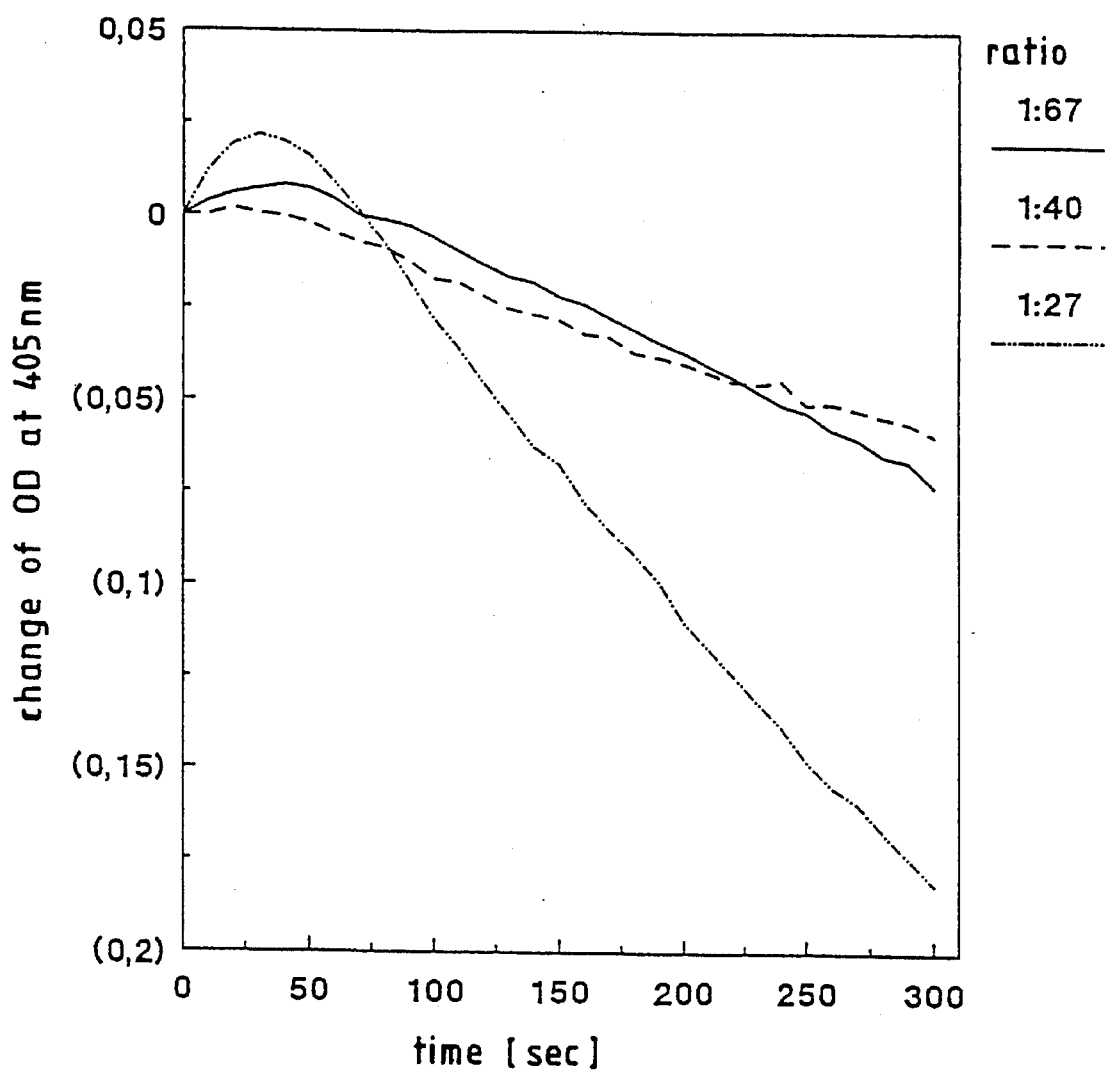

Kinetics of the reaction of anti-IgE coated latex particles of a commercially available product with various concentrations of IgE in serum with the latex concentrations customarily used. The turbidity was measured at 405 nm in a Cobas Bio at intervals of 10 seconds for 5 minutes. The concentration of the reagent was 0.025% in the sample solution. The measured differences from the absorption after 0.5 seconds are depicted.

FIG. 2:

Kinetics of the reaction of anti-D dimer coated latex particles with various concentrations of D dimer in physiological saline solution with the latex concentrations customarily used. The turbidity was measured at 405 nm in a Cobas Bio at intervals of 10 seconds for 5 minutes. The concentration of the reagent was 0.025% in the sample solution. The coupling ratio (antibody: latex) of the reagent was 1:40. The measured differences from the absorption after 0.5 seconds are depicted.

FIG. 3:

Dependence of the turbidity signal on the density of sensitized particles in the reaction medium. Latex particles coated with anti-D dimer (coupling ratio 1:40) were diluted in physiological saline solution to concentrations of 0.025, 0.1 and 0.2%. The reaction kinetics with a D dimer solution (250 µg/l) were measured at 405 nm in a Cobas Bio at intervals of 10 seconds for 5 minutes. The measured differences from the absorption after 0.5 seconds are depicted.

FIG. 4:

Kinetics of the reaction of anti-IgE coated latex particles of a commercially available product with various concentrations of IgE in serum by the method according to the invention. The turbidity was measured at 405 nm in a Cobas Bio at intervals of 10 seconds for 5 minutes. The concentration of the reagent was 0.2% in the sample solution. The measured differences from the absorption after 0.5 seconds are depicted.

FIG. 5:

Kinetics of the reaction of anti-D dimer coated latex particles with various concentrations of D dimer in physiological saline solution by the method according to the invention. The turbidity was measured at 405 nm in a Cobas Bio at intervals of 10 seconds for 5 minutes. The concentration of the reagent employed (coupling ratio 1:40) was 0.2%. The measured differences from the absorption after 0.5 seconds are depicted.

FIG. 6:

Dependence of the turbidity signal on the loading density of latex particles with anti-D dimer antibodies. Latex particles were coated with a monoclonal antibody against D dimer in the ratio of 1:67, 1:40 and 1:29 by the method described in Example 1. The reagents were employed in a concentration of 0.2%. The measured differences from the absorption after 0.5 seconds, which were measured with a D dimer solution (125 μg/l) at 405 nm in a Cobas Bio at intervals of 10 seconds for 5 minutes, are depicted.

I claim:

1. A method for determining the concentration of an analyte within less than 8 minutes comprising the steps of:
    a) mixing and distributing in an automatic centrifugal analyzer a sample of a biological material containing the analyte with at least one binding partner specific for the analyte, said binding partner being immobilized on a particulate carrier material wherein the concentration of the particulate carrier material in the mixture is higher than 0.09% by weight,
    b) maintaining constant centrifugal acceleration between 10 and 10,000 x g during the mixing and distributing step,
    c) determining a decrease in absorption as a measurement of turbidity immediately upon completion of the mixing and distributing step, and
    d) determining the concentration of the analyte by comparing the measurement of turbidity obtained in step c) with values measured under identical conditions for samples of known analyte content.

2. The method as claimed in claim 1, wherein the analyte and the specific binding partner are partners in an immunochemical reaction.

3. The method as claimed in claim 1, wherein particulate polymers selected from the group consisting of spherical natural and synthetic polymers are used as the particulate carrier material.

4. The method as claimed in claim 1, wherein the decrease in the absorption is measured at an angle of 0° to 180° to the direction of sedimentation.

5. The method as claimed in claim 1, wherein wavelengths from the range from 280 to 900 nm are used to measure the change in absorption.

6. The method as claimed in claim 1, wherein a fibrin degradation product D dimer protein or peptide thereof is used as the analyte and an antibody against the fibrin degradation product D dimer is used as the specific binding partner.

7. The method as claimed in claim 1, wherein styrene/methacrylic acid or methacrylate/methacrylic acid copolymers are used as the particulate carrier material.

8. The method as claimed in claim 1, wherein the centrifugal acceleration is in the range between 100–2,000 x g.

9. The method as claimed in claim 1, wherein the centrifugal acceleration is in the range between 800–1,200 x g.

10. The method as claimed in claim 1, wherein the concentration of the particulate carrier material is from 0.1 and 1% by weight.

* * * * *

UNITED STATES PATENT AND TRADEMARK OFFICE
CERTIFICATE OF CORRECTION

PATENT NO. : 5,571,728
DATED : November 05, 1996
INVENTOR(S) : Michael KRAUS

It is certified that error appears in the above-indentified patent and that said Letters Patent is hereby corrected as shown below:

Claim 5, Column 12, Line 13, "change" should read --decrease--.

Signed and Sealed this

Twenty-ninth Day of April, 1997

Attest:

BRUCE LEHMAN

*Attesting Officer*  Commissioner of Patents and Trademarks